United States Patent [19]

Langhauser et al.

[11] Patent Number: 5,585,509

[45] Date of Patent: Dec. 17, 1996

[54] METALLOCENE COMPLEXES HAVING HETEROFUNCTIONAL GROUPS IN THE CYCLOPENTADIENYL SYSTEM

[75] Inventors: Franz Langhauser, Bad Dürkheim; David Fischer, Gönnheim; Jürgen Kerth, Carlsberg; Günther Schweier, Friedelsheim, all of Germany; Hans-Herbert Brintzinger, Taegerswilen, Switzerland; Elke Barsties; Werner Roell, both of Konstanz, Germany

[73] Assignee: BASF Aktiengesellschaft, Ludwigshafen, Germany

[21] Appl. No.: 396,707

[22] Filed: Mar. 1, 1995

[30] Foreign Application Priority Data

Mar. 3, 1994 [DE] Germany .................. 44 06 963.4

[51] Int. Cl.$^6$ ................ C07F 17/00; C07F 9/00; C07F 9/02; C07F 7/22; C07F 7/28; C07F 7/30

[52] U.S. Cl. .............. 556/11; 556/12; 556/14; 556/22; 556/28; 556/30; 556/43; 556/53; 556/56; 556/87; 556/404; 556/431; 526/160; 526/161; 526/166; 526/169; 526/943; 548/402; 548/406; 548/400; 502/152; 502/162; 568/7; 585/350

[58] Field of Search ................ 556/11, 12, 14, 556/22, 28, 30, 43, 53, 56, 87, 404, 431; 568/7; 585/350; 502/152, 162; 526/160, 161, 166, 169, 943; 548/402, 406, 400

[56] References Cited

U.S. PATENT DOCUMENTS 5,296,434 3/1994 Karl et al. ................ 502/117

FOREIGN PATENT DOCUMENTS 2036824 8/1991 Canada .
444474 9/1991 European Pat. Off. .
519237 12/1992 European Pat. Off. .

OTHER PUBLICATIONS

I. M. Lee et al., Organometallics 11 (1992) 2115–2122.
Hortmann et al., New J. Chem. 16 (1992), 51–55.
Spaleck et al., Angew, Chemie 104 (1992), 1373–1376.
Ewen et al., Makromol. Chem., Makromol. Symp. 48/49 (1991), 253–295.

Primary Examiner—Porfirio Nazario-Gonzalez
Attorney, Agent, or Firm—Keil & Weinkauf

[57] ABSTRACT

Metallocene complexes of the general formula I

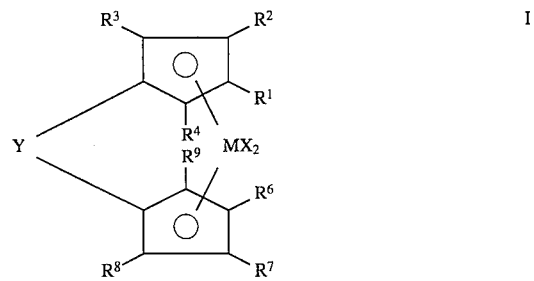

where the substituents Y, M, x, $R^1$, $R^2$, $R^3$, $R^4$, $R^6$, $R^7$, $R^8$, and $R^9$ are as described in the disclosure, and ligand systems of the general formula II

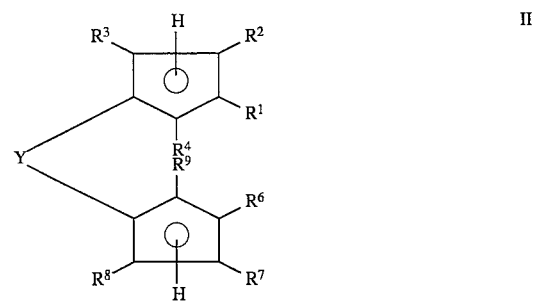

as intermediates.

4 Claims, No Drawings

METALLOCENE COMPLEXES HAVING HETEROFUNCTIONAL GROUPS IN THE CYCLOPENTADIENYL SYSTEM

The present invention relates to metallocene complexes of the general formula I

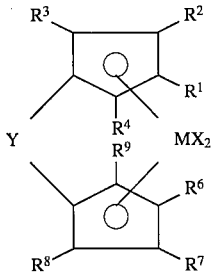

where

M is titanium, zirconium, hafnium, vanadium, niobium or tantalum,

X is fluorine, chlorine, bromine, iodine, hydrogen, $C_1$–$C_{10}$-alkyl, $C_6$–$C_{15}$-aryl or —$OR^5$, $R^5$ is $C_1$–$C_{10}$-alkyl, $C_6$–$C_{15}$-aryl, alkylaryl, arylalkyl, fluoroalkyl or fluoroaryl, each having 1 to 10 carbon atoms in the alkyl radical and 6 to 20 carbon atoms in the aryl radical, $R^1$ to $R^3$ and $R^6$ to $R^8$ are each hydrogen, $C_1$–$C_{10}$-alkyl or 5-membered to 7-membered cycloalkyl which in turn may carry $C_1$–$C_{10}$-alkyl substituents, or are each $C_6$–$C_{15}$-aryl or arylalkyl, where two neighboring radicals together may furthermore be a cyclic group of 4 to 15 carbon atoms, or $Si(R^{10})_3$, $R^{10}$ is $C_1$–$C_{10}$-alkyl, $C_6$–$C_{15}$-aryl or $C_3$–$C_{10}$-cycloalkyl, $R^4$ is

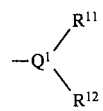

$Q^1$ is nitrogen, phosphorus, arsenic, antimony or bismuth, $R^{11}$ and $R^{12}$ are each $C_1$–$C_{10}$-alkyl, $C_3$–$C_{15}$-cycloalkyl, $C_6$–$C_{15}$-aryl, alkylaryl, arylalkyl, fluoroalkyl or fluoroaryl, each having 1 to 10 carbon atoms in the alkyl radical and 6 to 20 carbon atoms in the aryl radical, or the two radicals together may be a cyclic group of 2 to 15 carbon atoms which in turn may contain from 1 to 8 heteroatoms of main groups III to VI of the Periodic Table of Elements, $R^9$ is hydrogen, $C_1$–$C_{10}$-alkyl or 5-membered to 7-membered cycloalkyl which in turn may carry $C_1$–$C_{10}$-alkyl substituents, or is $C_6$–$C_{15}$-aryl or arylalkyl, where two neighboring radicals together may furthermore be a cyclic group of 4 to 15 carbon atoms, or $Si(R^{13})_3$ or

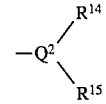

$R^{13}$ is $C_1$–$C_{10}$-alkyl, $C_6$–$C_{15}$-aryl or $C_3$–$C_{10}$-cycloalkyl, $Q^2$ is nitrogen, phosphorus, arsenic, antimony or bismuth, $R^{14}$ and $R^{15}$ are each $C_1$–$C_{10}$-alkyl, $C_3$–$C_{15}$-cycloalkyl, $C_6$–$C_{15}$-aryl, alkylaryl, arylalkyl, fluoroalkyl or fluoroaryl, each having 1 to 10 carbon atoms in the alkyl radical and 6 to 20 carbon atoms in the aryl radical, or the two radicals together may be a cyclic group of 2 to 15 carbon atoms which in turn may contain 1 to 8 heteroatoms of main groups III to VI of the Periodic Table of Elements, Y is

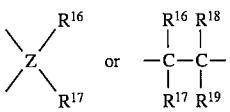

Z is silicon, germanium, tin or carbon, and $R^{16}$, $R^{17}$, $R^{18}$ and $R^{19}$ are each hydrogen, $C_1$–$C_{10}$-alkyl, $C_3$–$C_{10}$-cycloalkyl or $C_6$–$C_{15}$-aryl, where two neighboring radicals together may furthermore be a cyclic group of 4 to 15 carbon atoms.

The present invention furthermore relates to ligand systems of the general formula II

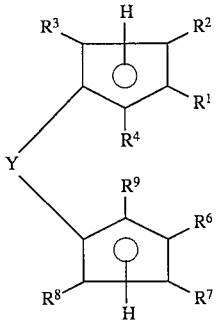

and a process for the preparation of such metallocene complexes I and ligand systems II, the use of the ligand systems II for the preparation of the metallocene complexes I, the use of the metallocene complexes I as catalysts for the polymerization of alkenes and processes for the preparation of such polymers using metallocene complexes I, the use of the polymers thus prepared for the production of fibers, films and moldings, and the fibers, films and moldings obtainable thereby.

J. A. Ewen et al., Makromol. Chem., Makromol. Symp. 48/49 (1991), 253–295, discloses that, when metallocenes are used as catalysts for olefin polymerization, the polymer properties can be influenced by varying the ligands. K. Hortmann, H. H. Brintzinger, New J. Chem. 16 (1992), 51–55, discusses steric effects and I. M. Lee et al., Organometallics 11 (1992), 2115–2122, discusses electronic effects as possibilities for influencing the substituents on the ligand. In EP-A 444 474 and EP-A 519 237, the ligands are varied by introducing different substituents in the cyclopentadienyl radical, such as alkyl or aryl substituents or benzofused systems. W. Spaleck et al., Angew. Chemie 104 (1992), 1373–1376, discloses variations in the bridge in chiral stereorigid metallocenes for the polymerization of prochiral olefins.

In these known metallocenes, either electronic or steric effects, but not both effects simultaneously, are obtained by the particular variation.

It is an object of the present invention to provide metallocene complexes which can be used as catalysts for olefin polymerization and which can influence the polymer properties both by electronic and by steric effects.

We have found that this object is achieved by the metallocene complexes I defined at the outset.

We have also found ligand systems II and processes for the preparation of such metallocene complexes I and ligand systems II, the use of the ligand systems II for the preparation of the metallocene complexes I, the use of the metallocene complexes I as catalysts for the polymerization of alkenes and processes for the preparation of such polymers using metallocene complexes I, the use of the polymers thus prepared for the production of fibers, films and moldings, and fibers, films and moldings obtainable thereby.

Preferred novel metallocene complexes of the general formula I

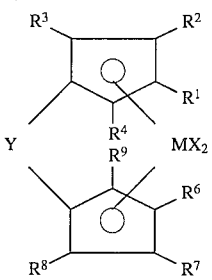   I are those in which:
M is titanium, zirconium or hafnium,
X is chlorine or $C_1$–$C_4$-alkyl,
$R^1$ to $R^3$ and $R^6$ to $R^8$ are each hydrogen, $C_1$–$C_6$-alkyl, or phenyl, where two neighboring radicals together are a cyclic group of 4 to 12 carbon atoms, in particular indenyl, $C_1$–$C_4$-alkyl-substituted indenyl or benzindenyl, and $R^1$ and $R^6$ preferably have the same meaning, as do $R^2$ and $R^7$ as well as $R^3$ and $R^8$
$Q^1$ is nitrogen, phosphorus or arsenic,
$R^{11}$ and $R^{12}$ are preferably identical and are $C_1$–$C_6$-alkyl or the two radicals together are a cyclic group of 2 to 8 carbon atoms which in turn may contain 1 to 6, in particular 1 to 4, heteroatoms of main groups III to VI of the Periodic Table of Elements, P and N being preferred,
$R^4$ is dimethylamino or pyrrolidino,
$R^9$ is preferably identical to $R^4$,
Y is

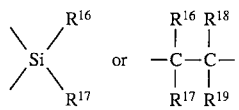

and
$R^{16}$, $R^{17}$, $R^{18}$ and $R^{19}$ are each hydrogen or $C_1$–$C_6$-alkyl.

Particularly preferred metallocene complexes I are: dimethylsilanediylbis(2-N,N-dimethylamino-4-tert-butylcyclopentadienyl)zirconium dichloride, dimethylsilanediylbis(2-N,N-dimethylamino-4-phenylcyclopentadienyl)zirconium dichloride, dimethylsilanediylbis(2-N,N-dimethylamino-4-isopropylcyclopentadienyl)zirconium dichloride, dimethylsilanediylbis(2-N,N-dimethylamlno-4-tert-butylcyclopentadienyl)titanium dichloride, dimethylsilanediylbis(2-N,N-dimethylamlno-4-tert-butylcyclopentadienyl)hafnium chloride, dimethylsilanediylbis(2-N,N-dimethylamlno-4-tert-butylcyclopentadienyl)zirconiumdimethyl, dimethylsilanediylbis(2-N,N-dimethylamino-4-tert-butylcyclopentadienyl)hafniumdimethyl, dimethylsilanediylbis(2-N,N-dimethylamino-4-tert-butylcyclopentadienyl)titaniumdimethyl, dimethylsilanediylbis(2-N,N-dimethylaminoindenyl)titanium dichloride, dimethylsilanediylbis(2-N,N-dimethylaminoindenyl)zirconium dichloride, dimethylsilanediylbis(2-N,N-dimethylaminoindenyl)hafnium dichloride, dimethylsilanediylbis(2-N,N-dimethylaminobenzindenyl)titanium dichloride, dimethylsilanediylbis(2-N,N-dimethylaminobenzindenyl)zirconium dichloride, dimethylsilanediylbis(2-N,N-dimethylaminobenzindenyl)hafnium dichloride, dimethylsilanediylbis(2-pyrrolidinoindenyl)titanium dichloride, dimethylsilanediylbis(2-pyrrolidinoindenyl)zirconium dichloride, dimethylsilanediylbis(2-pyrrolidinoindenyl)hafnium dichloride, dimethylsilanediylbis(2-pyrrolidinobenzindenyl)titanium dichloride, dimethylsilanediylbis(2-pyrrolidinobenzindenyl)zirconium dichloride and dimethylsilanediylbis(2-pyrrolidinobenzindenyl)hafnium dichloride.

The novel metallocene complexes I can be prepared in such a way that the ligand systems II

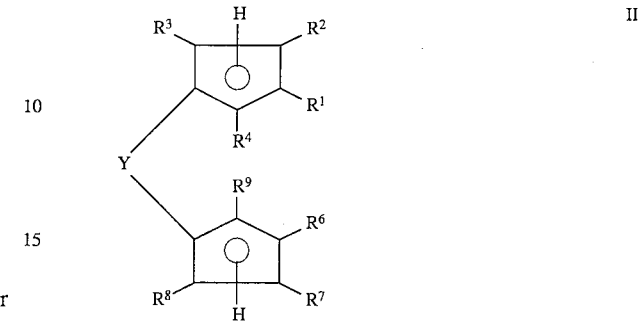

occur as intermediates. Regarding the preferred substituents, the statements made in the case of the metallocene complexes I are applicable.

A preferred process for the preparation of the metallocene complexes I and hence also for the preparation of the ligand systems II is the following:

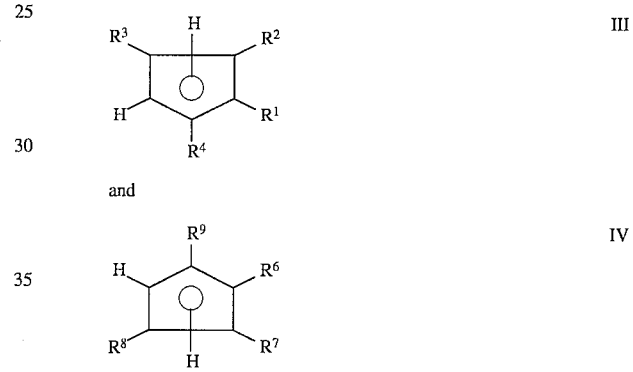

are reacted with a metallating agent, such as an alkali metal alkyl, an alkaline earth metal alkyl, an alkali metal hydride or an alkaline earth metal hydride, preferably n-butyllithium, methyllithium or potassium hydride, and then with $Y(X^1)_2$, where $X^1$ is fluorine, chlorine, bromine or iodine, preferably chlorine, and the ligand systems II are thus obtained.

The reaction conditions are in principle not critical. Usually, an organic solvent, such as an ether and/or a hydrocarbon, preferably diethyl ether or tetrahydrofuran (THF) is added to III and IV and the mixture is cooled to temperatures of from −80° to 0° C. The metallating agent, preferably n-butyllithium, to which a solvent, such as hexane, has preferably been added, is then introduced. After heating to room temperature, $Y(X^1)_2$, to which an organic solvent, such as diethyl ether or THF, has likewise been added, is introduced. Working up is carried out by precipitation or crystallization.

The ligand systems II can then likewise be reacted with a metallating agent, such as an alkali metal alkyl, an alkaline earth metal alkyl, an alkali metal hydride or an alkaline earth metal hydride, preferably n-butyllithium, and then with $MX_4$, the novel metallocene complexes I being formed.

The reaction conditions for the preparation of the metallocene complexes I are also not critical; in a preferred procedure, an organic solvent, such as an ether, preferably diethyl ether, is added to II and the mixture is cooled to temperatures of from −80° to 0° C. The metallating agent, to which a solvent, such as hexane, has preferably been added, is then introduced. After heating to room temperature and adding a hydrocarbon, preferably pentane, as a nonpolar solvent, the corresponding ligand-lithium salt can be separated off and isolated. This ligand-lithium salt is then preferably mixed with $MX_4$ under an inert gas atmosphere. The resulting isomer mixtures are separated into racemate and meso form by fractional crystallization from a conventional solvent, such as a hydrocarbon, an ether or a halohydrocarbon or a mixture thereof.

The novel metallocene complexes I may be used as catalysts for the polymerization of alkenes and they may influence the polymer properties both by electronic and by steric effects.

In a preferred procedure, the metallocene complexes I are reacted with a quaternizing agent of the general formula V $$A_aX^2 \qquad\qquad V$$

where

A is $C_1$–$C_{10}$-alkyl, $C_3$–$C_{15}$-cycloalkyl, $C_6$—$C_{15}$-aryl, alkylaryl, arylalkyl, fluoroalkyl or fluoroaryl, where each alkyl radical is of 1 to 10 carbon atoms and each aryl radical is of 6 to 20 carbon atoms, $X^2$ is fluorine, chlorine, bromine, iodine, $SO_3{}^2$—, $SO_4{}^2$— or $NO_3$—, and a is 1 or 2.

Preferred compounds of the general formula V are $C_1$—$C_6$-alkyl halides, in particular methyl iodide, and $C_6$—$C_{10}$-aryl halides, in particular 2,4,6-trimethylbenzyl chloride.

The reaction conditions are in principle not critical. Usually, the reaction is carried out by adding an organic solvent, such as an aromatic hydrocarbon, preferably toluene, to the metallocene complex I and introducing the quaternizing agent, preferably at room temperature.

If $R^9$ is

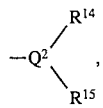

quaternized metallocene complexes I' are thus obtained from the metallocene complexes I:

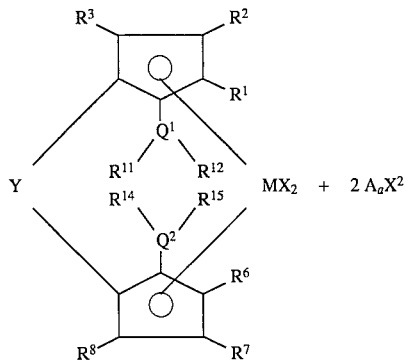

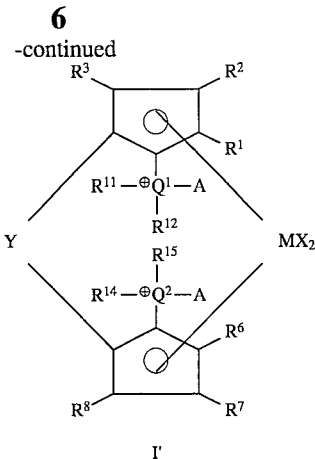

These quaternized metallocene complexes I' can be produced in situ and can be used in combination with a cocatalyst, preferably with an open-chain or cyclic alumoxane compound of the general formula VI or VII

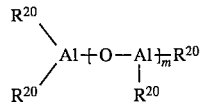 VI

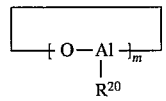 VII where $R^{20}$ is $C_1$–$C_4$-alkyl, preferably methyl or ethyl, and m is an integer from 5 to 30, preferably from 10 to 25, for the polymerization of $C_2$–$C_{10}$-alk-1-enes.

The preparation of these oligomeric alumoxane compounds VI or VII is usually carried out by reacting a solution of a trialkylaluminum with water and is described in, inter alia, EP-A 284 708 and U.S. Pat. No. 4,794,096.

As a rule, the oligomeric alumoxane compounds obtained are present as mixtures of both linear and cyclic chain molecules of different lengths, so that m is to be regarded as an average value. The alumoxane compound may also be present as a mixture with other metal alkyls, preferably with aluminum alkyls.

It has proven advantageous to use the quaternized metallocene complexes I' and the oligomeric alumoxane compound in amounts such that the atomic ratio of aluminum from the oligomeric alumoxane compound to the transition metal from the quaternized metallocene complex I' is from 10:1 to $10^{6}$:1, in particular from 10:1 to $10^4$:1.

In the preparation of the polymers of $C_2$–$C_{10}$-alk-1-enes, it is also possible to use a supported catalyst system. Suitable carriers are, for example, silica gels, preferably those of the formula $SiO_2$. b $Al_2O_3$, where b is from 0 to 2, preferably from 0 to 0.5; these are therefore aluminosilicates or silica. The carriers preferably have a particle diameter of from 1 to 200 μm, in particular from 30 to 80 μm. Such products are commercially available, for example silica gel 332 from Grace. Further carriers include finely divided polyolefins, for example finely divided polypropylene.

Polymers of $C_2$–$C_{10}$-alk-1-enes are to be understood as meaning homopolymers or copolymers of $C_2$–$C_{10}$-alk-1-enes, in particular of $C_2$–$C_6$-alk-1-enes. Homopolymers of ethylene or of propylene and copolymers of ethylene and propylene, ethylene and but-1-ene, ethylene and pent-1-ene, ethylene and hex-1-ene, propylene and but-1-ene, propylene and pent-1-ene as well as propylene and hex-1-ene, are preferred. The amount of comonomers may be up to 50, in particular up to 30%, by weight.

The novel process can be carried out in solution, in suspension, in the gas phase or as mass polymerization. The process for the preparation of the polymers of $C_2$–$C_{10}$-alk-1-enes is preferably carried out in solution or in the gas phase. The polymerization conditions are in principle not critical; pressures of from 0.5 to 3000, preferably from 1 to 80, bar and temperatures of from −50° to +300° C., preferably from 0° to 150° C., have proven suitable. The polymerization can be carried out in the presence of conventional regulators, for example hydrogen or $C_2$–$C_8$-alk-1-enes, and in conventional polymerization reactors.

In a preferred process for the preparation of homopolymers of $C_2$–$C_{10}$-alk-1-enes, the active components of the catalyst system are initially taken in toluene at from 0° to 140° C.

The $C_2$–$C_{10}$-alk-1-ene is then added to said initially taken components over a period of from 0.5 to 12 hours at from 1 to 60 bar. The polymers are then worked up by a conventional method.

The process described for the preparation of polymers of $C_2$–$C_{10}$-alk-1-enes does not involve expensive process engineering.

The $C_2$–$C_{10}$-alk-1-ene polymers prepared by the process described have a balanced property profile, in particular a high molecular weight, a narrow molecular weight distribution and high stereo-specificity and are suitable for the production of fibers, films and moldings.

EXAMPLES

EXAMPLE 1

Preparation of Dimethylsilanediylbis(2-N,N-dimethylaminoindenyl)-zirconium Dichloride I1

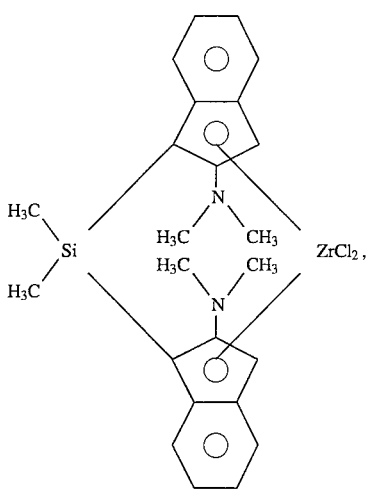

a) Preparation of the ligand system bis(2-N,N-dimethylaminoindenyl)dimethylsilane II1

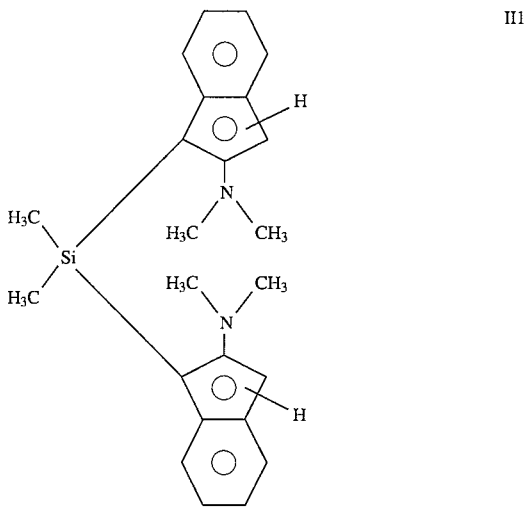

5.69 g ($\hat{=}$ 36 mmol) of 2-N,N-dimethylaminoindene III1 were dissolved in 100 ml of diethyl ether and the solution was cooled to −10° C. 22.4 ml ($\hat{=}$ 36 mmol) of a 1.6 molar solution of n-butyllithium in hexane were added and, after thawing was complete, stirring was carried out for 8 hours at room temperature. Thereafter, 2.24 ml ($\hat{=}$ 18 mmol) of dimethyldichlorosilane in 20 ml of diethyl ether were added and stirring was continued for a further 18 hours. The precipitated lithium chloride was filtered off and the filtrate was evaporated to half its volume and cooled to −80° C. 3.24 g ($\hat{=}$ 14 mmol, 48% of theory) of II1 were obtained as a slightly gray, finely crystalline precipitate. $^1$H-NMR (CDCl$_3$, δ rel TMS):

| d [ppm] (Mult) | Number | J [Hz] | Assignment |
|---|---|---|---|
| −1.59 (s) | | | |
| −0.41 (s) | 6 | | |
| −0.23 (s) | | | Si(CH$_3$)$_3$ |
| 2.77 (s) | 12 | 17.7 | N(CH$_3$)$_2$ |
| 3.93 (d) | 2 | 16.9 | H in five-membered ring |
| 5.63 (d) | 2 | | H in five-membered ring |
| 6.8–7.4 (m, broad) | 8 | | Aromat. H | b) Conversion of III1 to I1

7.56 g ($\hat{=}$ 47 mmol) of II1 were dissolved in 250 ml of diethyl ether and the solution was cooled to −10° C. 58.75 ml (= 94 mmol) of a 1.6 molar solution of n-butyllithium in hexane were added. After the mixture had been stirred for 2 hours at room temperature, 100 ml of n-pentane were added, stirring was continued for a further hour and the mixture was then filtered. 17.21 g ($\hat{=}$ 44.5 mmol, 94.7% of theory) of the ligand-lithium salt were obtained.

3 g ($\hat{=}$ 7.7 mmol) of this ligand-lithium salt were dry-blended with 1.79 g ($\hat{=}$ 7.7 mmol) of ZrCl$_4$ under an inert gas atmosphere. 100 ml of toluene were added to this, and the brownish yellow suspension was stirred for 18 hours at room temperature. The supernatant solution was removed and was evaporated to dryness under reduced pressure from an oil pump. This gave 1 g ($\hat{=}$ 1.8 mmol, 24% of theory) of I1 having a ratio of racemate to meso form of 3:1.

The residue from the reaction batch was extracted with 150 ml of methylene chloride, and the extract was filtered and cooled to −80° C. 1.5 g ($\hat{=}$ 2.4 mmol, 36% of theory) of I1 crystallized from this solution. 0.7 g of pure rac-I1 was obtained by recrystallization from methylene chloride/diethyl ether (volume ratio 1:9) at −80° C. (cf. FIG. 1: crystal structure of I1) $^1$H-NMR (CDCl$_3$, δ rel TMS):

| d [ppm] (Mult) | Number | Assignment |
| --- | --- | --- |
| Racemic compound | | |
| 1.29 (s) | 6 | Si(CH$_3$)$_2$ |
| 2.61 (s) | 12 | N(CH$_3$)$_2$ |
| 6.39 (s) | 2 | Cp-H |
| 6.74–7.55 (m, broad) | 8 | Aromat.-H |
| Meso compound | | |
| 1.32 (s) | 3 | Si(CH$_3$)$_2$ |
| 1.36 (s) | 3 | Si(CH$_3$)$_2$ |
| 2.80 (s) | 12 | N(CH$_3$)$_2$ |
| 6.40 (s) | 2 | Cp-H |
| 6.74–7.55 (m, broad) | 8 | Aromat.-H |

Mass spectrum (EI, 70 eV, 220° C.) m/e=534 (M$^+$, 22.3%), 376 (M$^+$- C$_9$H$_6$N(CH$_3$)$_2$, 14.9%).

EXAMPLE 2

Preparation of Dimethylsilanediylbis(2-pyrrolidino-1-indenyl)zirconium Dichloride I2

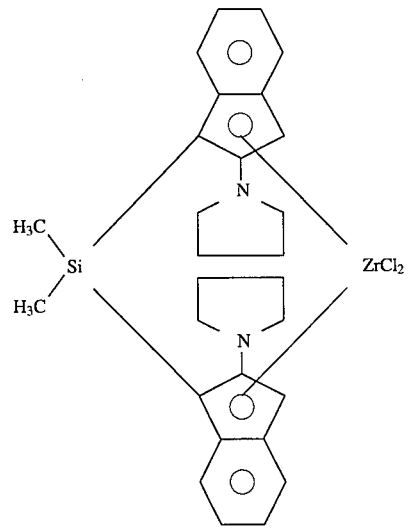

a) Preparation of the Ligand System bis(2-pyrrolidino-1-indenyl)dimethylsilane II2

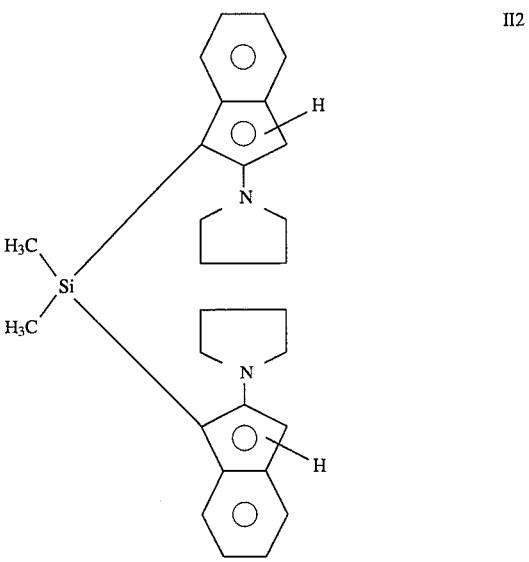

50.6 ml ($\hat{=}$ 81 mmol) of a 1.6 molar solution of n-butyllithium in hexane were added to a solution of 15 g ($\hat{=}$ 81 mmol) of 2-pyrrolidino-1-indene III2 in 250 ml of THF, which solution had been cooled to −78° C. After. the addition, stirring was carried out for a further 30 minutes at −78° C. and for a further 2 hours at room temperature. Thereafter, 4.9 ml ($\hat{=}$ 40 mmol) of dimethyldichlorosilane in 50 ml of THF were added and stirring was continued for a further 16 hours. The solvent was removed under reduced pressure from an oil pump, the residue was taken up in 200 ml of diethyl ether and stirred for 90 minutes, the mixture was then filtered and the filtrate was cooled to −80° C. 7.76 g ($\hat{=}$ 18 mmol, 45% of theory) of II2 were obtained as a gray powder. $^1$H-NMR (CDCl$_3$, δ rel TMS):

| d [ppm] (Mult) | Number | J [Hz] | Assignment |
| --- | --- | --- | --- |
| racemic compound | | | |
| −0.67 (s) | | | Si(CH$_3$)$_2$ |
| −0.50 (s) | 6 | | |
| −0.25 (s) | | | |
| 1.65–1.95 (m, broad) | 8 | | Pyrrolidine-β-H |
| 2.94–3.17 (m, broad) | 8 | | Pyrrolidine-α-H |
| 3.81 (d) | 2 | 16.6 | Cp-H |
| 5.63 (d) | 2 | 3.6 | Cp-H |
| 6.92–7.34 (m, broad) | 8 | | Aromatic | b) Conversion of II2 to I2

23.7 ml (≙ 38 mmol) of a 1.6 molar solution of n-butyllithium in hexane were added to a solution of 8.1 g (≙ 19 mmol) of II2 in 250 ml of diethyl ether, which solution had been cooled to −70° C. After the addition, stirring was carried out for a further 30 minutes at −70° C. and for a further 2 hours at room temperature. Thereafter, 100 ml of n-pentane were added, stirring was carried out for a further hour, the mixture was filtered and the precipitate was dried under reduced pressure from an oil pump. 7.57 g (≙ 17 mmol, 91% of theory) of the ligand-lithium salt were obtained.

3 g (≙ 6.8 mmol) of this ligand-lithium salt were dry-blended with 1.68 g (≙ 6.8 mmol) of $ZrCl_4$ under an inert gas atmosphere. 100 ml of toluene were added to this and stirring was carried out for 18 hours at room temperature. The supernatant solution was removed and was evaporated to dryness under reduced pressure from an oil pump, 1.1 g (≙ 1.9 mmol, 27% of theory) of I2 having a ratio of racemate to meso form of 1:1.5 were obtained in this manner. The residue from the reaction batch was extracted with 150 ml of methylene chloride, filtered and cooled to −80° C. 0.7 g (≙ 1.2 mmol, 18% of theory) of pure rac-I2 was obtained. $^1$H-NMR (CDCl$_3$, δ rel TMS):

| d [ppm] (Mult) | Number | Assignment |
|---|---|---|
| Racemic compound | | |
| 1.25 (s) | 6 | Si(CH$_3$)$_2$ |
| 1.72–1.77 (m) | 8 | Pyrrolidine-β-H |
| 3.10–3.97 (m) | 8 | Pyrrolidine-α-H |
| 6.21 (s) | 2 | Cp-H |
| 7.00–7.60 (m, broad) | 8 | Aromat.-H |
| Meso compound | | |
| 1.19 (s) | 3 | Si(CH$_3$)$_2$ |
| 1.38 (s) | 3 | Si(CH$_3$)$_2$ |
| 1.77–1.89 (m) | 8 | Pyrrolidine-β-H |
| 3.17–3.30 (m) | 8 | Pyrrolidine-α-H |
| 6.21 (s) | 8 | Cp-H |
| 7.00–7.60 (m, broad) | 8 | Aromat.-H |

Mass spectrum (El, 70 eV, 220° C. m/e=586 (M$^+$, 76%))

EXAMPLES 3 AND 4

Preparation of Polypropylene (PP) By Solution Polymerization

EXAMPLE 3

First 0.3 ml (≙ 4.8 mmol) of methyl iodide and then 2.5 ml (≙ 3.9 mmol) of a 10% strength by weight solution of methyl alumoxane in toluene were added to 1.97 mg (≙ 3.7 μmol) of I1 in 20 ml of toluene and the mixture was stirred for 90 minutes. After the addition of a further 200 ml of toluene, the mixture was heated to 50° .C and propylene was introduced at this temperature and at 1 bar. This pressure was kept constant during the entire polymerization time of 4.5 hours. To terminate the polymerization, the reaction mixture was poured into a solution of 500 ml of methanol and 5 ml of concentrated hydrochloric acid, and the precipitated PP was filtered off, washed several times with methanol and dried.

The properties of the resulting PP are listed in the table.

EXAMPLE 4

The procedure was as in Example 3, except that 1.67 mg (≙ 3.2 μmol) of I1 were used, and 50 mg (≙ 2.9 mmol) of 2,4,6-trimethylbenzyl chloride instead of the methyl iodide.

The properties of the resulting PP are likewise listed in the table.

| | Example 3 | Example 4 |
|---|---|---|
| Yield [g] | 0.92 | 0.40 |
| is Productivity [g/g of metallocene I1] | 467 | 239 |
| Melting point [°C.] | 130 | 133 |
| M$_w$ | 21,700 | 12,900 |
| M$_n$ | 10,300 | 8,260 |
| M$_w$:M$_n$ | 2.1 | 1.6 |
| mmmm-pentads [%] | 77 | 79 |

The melting points were determined by means of DSC measurements (10°/min heating rate). The weight average values M$_w$ and number average values M$_n$ were determined by gel permeation chromatography. The pentads were determined by means of $^{13}$C-NMR spectroscopy.

COMPARATIVE EXAMPLE VI

The procedure was as in Example 3 or Example 4, but without the addition of methyl iodide or 2,4,6-trimethylbenzyl chloride. In this case, no polymerization was observed.

EXAMPLE 5

Preparation of PP By Gas-phase Polymerization a) Preparation of the Supported Catalyst 0.1 ml (≙ 1.6 mmol) of methyl iodide was added to a solution of 15.4 mg (≙ 28.8 μmol) of I1 in 40 ml of toluene at room temperature and stirring was carried out for 1 hour. Thereafter, the solvent was stripped off completely under reduced pressure from an oil pump, 11.3 ml (= 17.2 mmol) of a 1.53 molar solution of methyl alumoxane in toluene were added to the remaining residue and preactivation was carried out for 15 minutes. 1.9 g of polypropylene powder having a mean particle diameter of 10 μm were then added as a carrier to this solution and stirring was carried out for a further 30 minutes. The volatile components were then removed under reduced pressure from an oil pump. 2.96 g of a free-flowing catalyst powder containing 15.2 μmol of catalyst/g of carrier were obtained.

b) Polymerization 20 g of sodium chloride and 5 ml of triethylaluminum (1 molar solution in heptane) were initially introduced in succession into a dry, nitrogen-flushed 10 l autoclave and stirred for 15 minutes. 2 g of the supported catalyst prepared according to a) were then introduced into the reactor with a nitrogen countercurrent, and the reactor was closed. At a stirrer speed of 350 rpm, the mixture was heated to 70° C. and at the same time the internal pressure was gradually increased to the final pressure of 28 bar by introducing propylene. Polymerization was then effected for 1.5 hours, fresh propylene being added by automatic pressure regulation. After the end of the reaction, the pressure was let down to atmospheric pressure in the course of 10 minutes and the resulting PP was discharged in a stream of nitrogen. In order to remove the sodium chloride, the polymer was washed several times with water and then with methanol and was dried in a drying oven at 80° C./20 mbar for 6 hours. 120 g of polypropylene powder were obtained.

Productivity: 11,500 g/g of metallocene I1 intrinsic viscosity [η]=1.34 dl/g (determined in decalin at 135° C.) Melting point: 143.5° C. $M_w$=171,200 $M_w$:$M_n$=3.1 mmmm-pentads: 91.2%

We claim:

1. A metallocene complex of the formula I

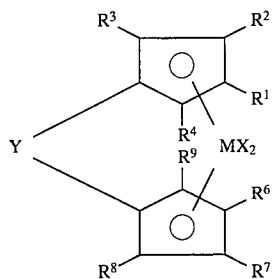

where

M is titanium, zirconium, hafnium, vanadium, niobium or tantalum,

X is fluorine, chlorine, bromine, iodine, hydrogen, $C_1$–$C_{10}$-alkyl, $C_6$–$C_{15}$-aryl or —$OR^5$, $R^5$ is $C_1$—$C_{10}$-alkyl, $C_6$–$C_{15}$-aryl, alkylaryl, arylalkyl, fluoroalkyl or fluoroaryl, each having 1 to 10 carbon atoms in the alkyl radical and 6 to 20 carbon atoms in the aryl radical, $R^1$ to $R^3$ and $R^6$ to $R^8$ are each hydrogen, $C_1$–$C_{10}$-alkyl or 5-membered to 7-membered cycloalkyl which in turn may carry $C_1$–$C_{10}$-alkyl substituents, or are each $C_6$–$C_{15}$-aryl or arylalkyl, where two neighboring radicals together may furthermore be a cyclic group of 4 to 15 carbon atoms, or $Si(R^{10})_3$, $R^{10}$ is $C_1$–$C_{10}$-alkyl, $C_6$–$C_{15}$-aryl or $C_3$–$C_{10}$-cycloalkyl, $R^4$ is

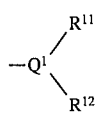

$Q^1$ is nitrogen, phosphorus, arsenic, antimony or bismuth, $R^{11}$ and $R^{12}$ are each $C_1$–$C_{10}$-alkyl, $C_3$–$C_{15}$-cycloalkyl, $C_6$–$C_{15}$-aryl, alkylaryl, arylalkyl, fluoroalkyl or fluoroaryl, each having 1 to 10 carbon atoms in the alkyl radical and 6 to 20 carbon atoms in the aryl radical, or the two radicals together may be a cyclic group of 2 to 15 carbon atoms which in turn may contain from 1 to 8 heteroatoms of main groups III to VI of the Periodic Table of Elements, $R^9$ is hydrogen, $C_1$–$C_{10}$-alkyl or 5-membered to 7-membered cycloalkyl which in turn may carry $C_1$–$C_{10}$-alkyl substituents, or is $C_6$–$C_{15}$-aryl or arylalkyl, where two neighboring radicals together may furthermore be a cyclic group of 4 to 15 carbon atoms, or $Si(R^{13})_3$ or

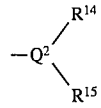

$R^{13}$ is $C_1$–$C_{10}$-alkyl, $C_6$–$C_{15}$-aryl or $C_3$–$C_{10}$-cycloalkyl, $Q^2$ is nitrogen, phosphorus, arsenic, antimony or bismuth, $R^{14}$ and $R^{15}$ are each $C_1$–$C_{10}$-alkyl, $C_3$–$C_{15}$-cycloalkyl, $C_6$–$C_{15}$-aryl, alkylaryl, arylalkyl, fluoroalkyl or fluoroaryl, each having 1 to 10 carbon atoms in the alkyl radical and 6 to 20 carbon atoms in the aryl radical, or the two radicals together may be a cyclic group of 2 to 15 carbon atoms which in turn may contain 1 to 8 heteroatoms of main groups III to VI of the Periodic Table of Elements, Y is

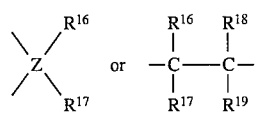

Z is silicon, germanium, tin or carbon, and $R^{16}$, $R^{17}$, $R^{18}$ and $R^{19}$ are each hydrogen, $C_1$–$C_{10}$-alkyl, $C_3$–$C_{10}$-cycloalkyl or $C_6$–$C_{15}$-aryl, where two neighboring radicals together may furthermore be a cyclic group of 4 to 15 carbon atoms.

2. A ligand system of the formula II

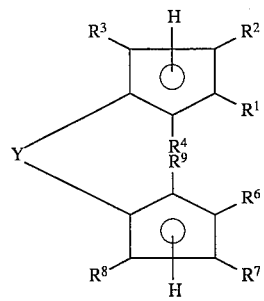

where $R^1$ to $R^3$ and $R^6$ to $R^8$ are each hydrogen, $C_1$–$C_{10}$-alkyl or 5-membered to 7-membered cycloalkyl which in turn may carry $C_1$–$C_{10}$-alkyl substituents, or are each $C_6$–$C_{15}$-aryl or arylalkyl, where two neighboring radicals together may furthermore be a cyclic group of 4 to 15 carbon atoms, or $Si(R^{10})_3$, $R^{10}$ is $C_1$–$C_{10}$-alkyl, $C_6$–$C_{15}$-aryl or $C_3$–$C_{10}$-cycloalkyl, $R^4$ is

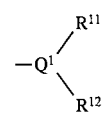

$Q^1$ is nitrogen, phosphorus, arsenic, antimony or bismuth, $R^{11}$ and $R^{12}$ are each $C_1$–$C_{10}$-alkyl, $C_3$–$C_{15}$-cycloalkyl, $C_6$–$C_{15}$-aryl, alkylaryl, arylalkyl, fluoroalkyl or fluoroaryl, each having 1 to 10 carbon atoms in the alkyl radical and 6 to 20 carbon atoms in the aryl radical, or the two radicals together may be a cyclic group of 2 to 15 carbon atoms which in turn may contain from 1 to 8 heteroatoms of main groups III to VI of the Periodic Table of Elements, $R^9$ is hydrogen, $C_1$–$C_{10}$-alkyl or 5-membered to 7-membered cycloalkyl which in turn may carry $C_1$–$C_{10}$-alkyl substituents, or is $C_6$–$C_{15}$-aryl or arylalkyl, where two neighboring radicals together may furthermore be a cyclic group of 4 to 15 carbon atoms, or $Si(R^{13})_3$ or

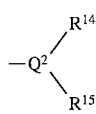

$R^{13}$ is $C_1$–$C_{10}$-alkyl, $C_6$–$C_{15}$-aryl or $C_3$–$C_{10}$-cycloalkyl, $Q^2$ is nitrogen, phosphorus, arsenic, antimony or bismuth, $R^{14}$ and $R^{15}$ are each $C_1$–$C_{10}$-alkyl, $C_3$–$C_{15}$-cycloalkyl, $C_6$–$C_{15}$-aryl, alkylaryl, arylalkyl, fluoroalkyl or fluoroaryl, each having 1 to 10 carbon atoms in the alkyl radical and 6 to 20 carbon atoms in the aryl radical, or the two radicals together may be a cyclic group of 2 to 15 carbon atoms which in turn may contain 1 to 8 heteroatoms of main groups III to VI of the Periodic Table of Elements, Y is

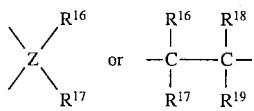

Z is silicon, germanium, tin or carbon, and $R^{16}$, $R^{17}$, $R^{18}$ and $R^{19}$ are each hydrogen, $C_1$–$C_{10}$-alkyl, $C_3$–$C_{10}$-cycloalkyl or $C_6$–$C_{15}$-aryl, where two neighboring radicals together may furthermore be a cyclic group of 4 to 15 carbon atoms.

3. A process for the preparation of a ligand system II as claimed in claim 2, which comprises reacting

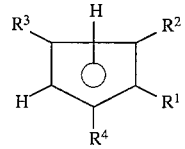

and

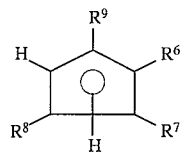

with a metallating agent and then with $Y(X^1)_2$, where $X^1$ is fluorine, chlorine, bromine or iodine.

4. A process for the preparation of a metallocene complex I as claimed in claim 1, which comprises reacting a ligand system of the formula II as defined in claim 2 with a metallating agent and then with $MX_4$.

* * * * *